United States Patent
Lee et al.

(10) Patent No.: US 9,435,771 B2
(45) Date of Patent: Sep. 6, 2016

(54) MULTI-FUNCTIONAL OPTION VALVE, MULTIFUNCTIONAL FULLY AUTOMATIC LIQUID CHROMATOGRAPHY SYSTEM INCLUDING THE SAME, AND METHOD FOR ANALYZING SAMPLE USING THE SAME

(75) Inventors: Sang-Won Lee, Seoul (KR); Seok-Won Hyung, Seoul (KR); Jung Hwa Lee, Bucheon (KR); Kyong-Chul Kim, Gyeonggi-Do (KR); Dong-Gi Mun, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 1193 days.

(21) Appl. No.: 13/397,409

(22) Filed: Feb. 15, 2012

(65) Prior Publication Data

US 2012/0145617 A1  Jun. 14, 2012

Related U.S. Application Data

(63) Continuation of application No. PCT/KR2011/004636, filed on Jun. 24, 2011.

(30) Foreign Application Priority Data

Jun. 25, 2010 (KR) .................. 10-2010-0060600

(51) Int. Cl.
*G01N 30/08* (2006.01)
*G01N 30/20* (2006.01)
*B01D 15/14* (2006.01)
*B01D 15/16* (2006.01)

(52) U.S. Cl.
CPC ............. *G01N 30/08* (2013.01); *B01D 15/14* (2013.01); *B01D 15/16* (2013.01); *G01N 30/20* (2013.01); *G01N 2030/085* (2013.01); *G01N 2030/201* (2013.01); *G01N 2030/202* (2013.01)

(58) Field of Classification Search
CPC ................. G01N 30/08; G01N 30/20; G01N 2030/201; G01N 2030/202; G01N 2030/085; C02F 1/008; C02F 1/28; C02F 1/281; C02F 1/283; C02F 1/285; C02F 1/286; C02F 1/288; C02F 2201/005; B01D 11/04; B01D 15/081; B01D 15/12; B01D 15/14; B01D 15/16; B01D 15/166; B01D 15/168; C07K 1/16; C07K 1/20
See application file for complete search history.

(56) References Cited

U.S. PATENT DOCUMENTS

| 5,105,851 A * | 4/1992 | Fogelman | G01N 30/20 137/625.11 |
| 2010/0024527 A1* | 2/2010 | LaMarr | B01D 15/14 73/61.56 |

*Primary Examiner* — Lucas Stelling
(74) *Attorney, Agent, or Firm* — Mintz Levin Cohn Ferris Glovsky and Popeo, P.C.; Kongsik Kim; Elaine V. Morlock

(57) ABSTRACT

Provided is a multifunction selection valve for use in a liquid chromatography system. The multifunction selection valve includes multiple ports to which both ends of a 1st dimension separation column may be connected at a part thereof, the multifunction selection valve including: a fluid passing mode in which a fluid introduced thereto is not passed through the 1st dimension separation column but is discharged; a column passing mode in which the fluid introduced thereto is passed through the 1st dimension separation column and then discharged; and a fluid blocking mode in which the fluid is prevented from being introduced. When using the multifunction selection valve, it modifies the flow paths of chromatographic solvents so that the resultant multifunctional liquid chromatography system allows one-dimensional separation, two-dimensional separation, on-line digestion and on-line phosphopeptide enrichment by a single binary pump.

20 Claims, 13 Drawing Sheets

MULTI-FUNCTIONAL OPTION VALVE, MULTIFUNCTIONAL FULLY AUTOMATIC LIQUID CHROMATOGRAPHY SYSTEM INCLUDING THE SAME, AND METHOD FOR ANALYZING SAMPLE USING THE SAME

CROSS REFERENCE TO RELATED APPLICATION

This application is a continuation of PCT/KR2011/004636 with the international filing date of Jun. 24, 2011, which claims priority to Korean Application No. 10-2010-0060600 filed on Jun. 25, 2010, which applications are incorporated herein by reference in their entirety.

TECHNICAL FIELD

The following disclosure relates to a multifunction selection valve. More particularly, the following disclosure relates to a multi-function selection valve which modifies the flow paths of chromatographic solvents so that the resultant multifunctional liquid chromatography system allows one-dimensional separation, two-dimensional separation, on-line digestion and on-line phosphopeptide enrichment by using a single binary pump. The following disclosure relates to the fully automated multifunctional liquid chromatography system including the function selection valve, and a method for analyzing a sample using the liquid chromatography system.

BACKGROUND

On-line solid phase extraction/capillary reverse-phase liquid chromatography has been used as a very important technological system in studying proteomes by virtue of its high efficiency in separation. Particularly, this allows efficient separation of trace amounts of biological substances and enables highly efficient identification of trace amounts of proteins due to its broad spectrum of analyte-solid phase interactions.

As a method for analyzing proteins, a mass spectrometry-based method has served as a standard analytic platform of proteomic study. A typical example of the method, such as a shot-gun method or a bottom-up method, includes hydrolysis of proteins into peptides prior to the analysis by a mass spectrometer. Such hydrolysis increases the solubilities of biological samples and produces peptide fragments that may be ionized and detected easily in a mass spectrometer.

However, the aforementioned method inevitably increases the complexity of samples. For example, in the case of one of the simplest proteomes, yeast proteome, 300,000 or more peptide fragments are produced from about 6,000 expressed proteins. Therefore, in order to overcome undersampling issue in analyzing the samples with enormous complexities, various methods including on-/off-line multidimensional protein identification technology have been developed (Link, A. J., Eng, J., Schieltz, D. M., Carmack, E., et al., *Nat. Biotechnol.* 1999, 17, 676-682; Chen, E. I., Hewel, J., Felding-Habermann, B., Yates, J. R. III, *Mol. Cell. Proteomics* 2006, 5, 53-56). However, improvement in the efficiency and sensitivity of a liquid chromatography column is still required. In this context, it has been known that the sensitivity of analysis based on liquid chromatography/mass spectrometry may be increased rapidly when the inner diameter of a separation column is decreased while maintaining the length thereof (Kim, M.-S., Choie, W.-S., Shin, Y. S., Yu, M. H., Lee, S.-W., *Bull. Korean Chem. Soc.* 2004, 25, 1833-1839).

In addition, in the case of a biological sample containing a significant amount of detergents and salts, an on-line desalting operation is an essential process required prior to mass spectrometry. This is because such impurities interrupt ionization of the peptide sample to be analyzed by a mass spectrometer, resulting in a drop in mass spectrometric detection sensitivity for the peptide sample. Thus, considering time saving and sample loss, on-line desalting is more suitable than off-line desalting.

Meanwhile, reverse-phase liquid chromatography systems according to the related art merely have a one-dimensional separation function of desalting and concentrating a sample by using a solid-phase extraction column. Even in the case of a two-dimensional reverse-phase liquid chromatography system carrying out a two-dimensional separation function by using a strong cation exchange chromatography system on-line linked to a reverse-phase liquid chromatography system, it is difficult to perform precise analysis due to mutual interference. Otherwise, such systems essentially require multiple solvent feed pumps, and thus have a complicated structure due to multiple valves for controlling the pumps. Moreover, such two-dimensional on-line reverse-phase liquid chromatography systems that also have Ion-line digestion function and online enrichment of phosphopeptides have never been reported or demonstrated before.

SUMMARY

An embodiment of the present disclosure is directed to providing a multifunction selection valve with which a reverse-phase liquid chromatography system realizes a function of reverse-phase one-dimensional separation capable of desalting and sample concentration; a function of two-dimensional separation function capable of increasing separation efficiency by linking one-dimensional separation using a 1st dimension separation column with reverse-phase two-dimensional separation; a function of on-line digestion capable of digestion of proteins into peptides by generating high pressure in chromatographic solvents; and a function of extracting phosphopeptides selectively by using a titanium dioxide column.

Another embodiment of the present disclosure is directed to providing a fully automated multifunctional liquid chromatography system using only one solvent feed pump and allowing automation of the aforementioned functions so that each function may be performed selectively by simple operation of the selection valve.

Still another embodiment of the present disclosure is directed to providing a method for analyzing a sample efficiently by using the aforementioned automated multifunctional liquid chromatography system.

In one general aspect, there is provided a multifunction selection valve having multiple ports to which both ends of a 1st dimension separation column may be connected at a part thereof, the multifunction selection valve including:
- a fluid passing mode in which a fluid introduced thereto is not passed through any columns but is discharged;
- a column passing mode in which the fluid introduced thereto is passed through the 1st dimension separation column and then discharged; and
- a fluid blocking mode in which the fluid is prevented from being introduced.

According to an embodiment, the multiple ports of the multifunction selection valve may include an inlet port, an outlet port, a first connecting port and a second connecting port linked individually to each end of the 1st dimension separation column, and multiple selection ports fluidically communicated with the other ports selectively to realize the above-described modes.

According to another embodiment, the inlet port may be fluidically communicated with the outlet port in the fluid passing mode; the inlet port may be fluidically communicated with the first connecting port of the 1st dimension separation column and the outlet port may be fluidically communicated with the second connecting port of the 1st dimension separation column in the column passing mode; and the inlet port and the outlet port may be fluidically interrupted with each other in the fluid blocking mode.

According to another embodiment, the multiple option ports of the multifunction selection valve may include a first, a second and a third selection ports; the second selection port may be fluidically communicated with the third selection port and the second connecting port of the 1st dimension separation column may be fluidically communicated with the first selection port, in the fluid passing mode; the second selection port may be fluidically communicated with the third selection port in the column passing mode; and the first connecting port of the 1st dimension separation column may be fluidically communicated with the second selection port, the second connecting port of the 1st dimension separation column may be fluidically communicated with the third selection port, and the first selection port may be fluidically communicated with the outlet port, in the fluid blocking mode.

In another general aspect, there is provided a multifunction selection valve having multiple ports to which both ends of a 1st dimension separation column may be connected at one part thereof and both ends of a titanium dioxide column may be connected at another part thereof, the multifunction selection valve including:
  a fluid passing mode in which a fluid introduced thereto is not passed through any columns but is discharged;
  a column passing mode in which the fluid introduced thereto is passed through the 1st dimension separation column and then discharged;
  a fluid blocking mode in which the fluid is prevented from being introduced; and
  a titanium dioxide column passing mode in which the fluid introduced thereto is passed through the titanium dioxide column and then discharged.

According to an embodiment, the multiple ports of the multifunction selection valve may include an inlet port, an outlet port, a first connecting port and a second connecting port linked individually to each end of the 1st dimension separation column, a first titanium dioxide column-connecting port and a second titanium dioxide column-connecting port that linked individually to each end of the titanium dioxide column, and multiple selection ports fluidically communicated with the other ports selectively to realize the above-described modes.

According to another embodiment, the inlet port may be fluidically communicated with the outlet port in the fluid passing mode; the inlet port may be fluidically communicated with the first connecting port of the 1st dimension separation column and the outlet port may be fluidically communicated with the second connecting port of the 1st dimension separation column in the column passing mode; the inlet port and the outlet port may be fluidically interrupted with the each other in the fluid blocking mode; and the inlet port may be fluidically communicated with the first titanium dioxide column-connecting port and the outlet port may be fluidically communicated with the second titanium dioxide column-connecting port, in the titanium dioxide column passing mode.

According to still another embodiment, the multiple selection ports may include a first, a second and a third selection ports; the first selection port may be fluidically communicated with the second titanium dioxide column-connecting port and the second selection port may be fluidically communicated with the third selection port, in the fluid passing mode; the first selection port may be fluidically communicated with the second titanium dioxide column-connecting port and the second selection port may be fluidically communicated with the third selection port, in the column passing mode; the first titanium dioxide column-connecting port may be closed, in the fluid blocking mode; and the first selection port may be fluidically communicated with the first connecting port of the 1st dimension separation column and the third selection port may be fluidically communicated with the second connecting port of the 1st dimension separation column, in the titanium dioxide column passing mode.

According to yet another embodiment, the 1st dimension separation column may be any one of a strong cation exchange column, a weak anion exchange column, a hydrophilic interaction liquid chromatography (HILIC) column and a strong cation exchange-weak cation exchange mixed column.

In still another general aspect, there is provided a fully automated multifunctional liquid chromatography system, including:
  a sample inlet valve to which a sample to be analyzed is introduced;
  a trap valve fluidically communicated with a solid phase extraction column and a reverse phase liquid chromatography column;
  a multifunction selection valve according to an embodiment, disposed in a flow path directing from the sample inlet valve to the trap valve; and
  a connection valve supplying the fluid discharged from the sample inlet valve selectively to the multifunction selection valve or the trap valve.

According to an embodiment, the liquid chromatography system may further include a solvent feed pump supplying the solvent to the sample inlet valve or the connection valve. A T-shaped solvent dividing tube may be connected to the solvent feed pump to supply the solvent selectively to the sample inlet valve or the connection valve.

According to still another embodiment, the sample inlet valve may include a sample inlet port, a sample outlet port, a first sample storage loop-connecting port and a second sample storage loop-connecting port linked to each other by a sample storage loop, a solvent inlet port, and a solvent outlet port. In addition, the sample inlet valve may include: a first mode in which the sample inlet port is fluidically communicated with the first sample storage loop-connecting port, and the second sample storage loop-connecting port is fluidically communicated with the sample outlet port; and a second mode in which the first sample storage loop-connecting port is fluidically communicated with the solvent outlet port, and the second sample storage loop-connecting port is fluidically communicated with the solvent inlet port.

According to still another embodiment, the connection valve may include a first inlet port, a second inlet port, a first connection port, a second connection port, a first outlet port and a second outlet port. In addition, the connection valve may include: a first mode in which the first inlet port, the first connection port, the second connection port and the first outlet port are fluidically communicated with one another in a sequential manner; and a second mode in which the second inlet port, the second connection port, the first connection port and the second outlet port are fluidically communicated with one another in a sequential manner.

According to still another embodiment, the connection valve may include a Z-shaped flow path formed among the fluidically communicated ports.

According to another embodiment, a function of one-dimensional separation of a sample is carried out, when the multifunction selection valve is in a fluid passing mode; a function of two-dimensional separation of a sample is carried out, when the multifunction selection valve is in a column passing mode; a function of on-line digestion is carried out, when the multifunction selection valve is in a fluid blocking mode; and a function of extracting phosphopeptides is carried out, when the multifunction selection valve is in a titanium dioxide column passing mode.

According to still another embodiment, the trap valve may include a solid phase extraction column-connecting port communicated with the solid phase extraction column, a reverse-phase liquid chromatography column-connecting port communicated with the reverse-phase liquid chromatography column, a first inlet port, a second inlet port, a sample conveying loop-connecting port linked to the solid phase extraction column-connecting port by a sample conveying loop, and an outlet port.

According to still another embodiment, the trap valve may include: a first mode in which the solid phase extraction column-connecting port is fluidically communicated with the first inlet port, and the sample conveying loop-connecting port is fluidically communicated with the outlet port; and a second mode in which the reverse-phase liquid chromatography column-connecting port is fluidically communicated with the solid phase extraction column-connecting port, and the second inlet port is fluidically communicated with the sample conveying loop-connecting port.

According to still another embodiment, the solvent outlet port of the sample inlet valve may be fluidically communicated with the first inlet port of the connection valve, the first outlet port of the connection valve may be fluidically communicated with the inlet port of the multifunction selection valve, the outlet port of the multifunction selection valve may be fluidically communicated with the first inlet port of the trap valve, and the second outlet port of the connection valve may be fluidically communicated with the second inlet port of the trap valve.

According to still another embodiment, the direction of the sample injected to the solid phase extraction column may be opposite to the direction of the sample eluted toward the reverse-phase liquid chromatography column.

According to still another embodiment, a solvent selection valve may be disposed in the solvent feed pump so as to supply either a first solvent or a mixed solvent of a first solvent with a second solvent.

In still another general aspect, there is provided a method for analyzing a sample by using the fully automated multifunctional liquid chromatography system according to an embodiment, the method including:
  (a) injecting a sample to be analyzed to the sample inlet valve;
  (b) setting the connection valve in such a mode that the sample inlet valve is fluidically communicated with the multifunction selection valve, and setting the multifunction selection valve in a fluid passing mode;
  (c) introducing a first solvent of the sample to the sample inlet valve so that the first solvent is injected to the solid-phase extraction column of the trap valve; and
  (d) changing the mode of the connection valve so that the sample inlet valve is fluidically communicated with the trap valve, and introducing a mixed solvent of the first solvent with a second solvent to the sample inlet valve so that the mixed solvent is injected to the solid-phase extraction column of the trap valve.

According to an embodiment, the mixed solvent passed through the solid-phase extraction column in step (d) is further passed through the reverse-phase liquid chromatography column so that the sample is analyzed.

According to another embodiment, the method may further include changing the mode of the multifunction selection valve into a column passing mode during step (c).

According to still another embodiment, the method may further include changing the mode of the multifunction selection valve into a titanium dioxide column passing mode, after changing the mode of the multifunction selection valve into a column passing mode.

In yet another general aspect, there is provided a method for analyzing a sample by using the fully automated multifunctional liquid chromatography system according to an embodiment, the method including:
  (a) injecting a sample to be analyzed to the sample inlet valve;
  (b) setting the connection valve in such a mode that the sample inlet valve is fluidically communicated with the multifunction selection valve, and setting the multifunction selection valve in a fluid blocking mode;
  (c) introducing a first solvent of the sample to the sample inlet valve so that the first solvent has an increased pressure;
  (d) changing the mode of the multifunction selection valve into a fluid passing mode and injecting the first solvent into the solid-phase extraction column of the trap valve; and
  (e) changing the mode of the connection valve so that the sample inlet valve is fluidically communicated with the trap valve, and introducing a mixed solvent of the first solvent with a second solvent to the sample inlet valve so that the mixed solvent is injected to the solid-phase extraction column of the trap valve.

According to an embodiment, the mixed solvent passed through the solid-phase extraction column in step (e) is further passed through the reverse-phase liquid chromatography column so that the sample is analyzed.

According to another embodiment, the method may further include changing the mode of the multifunction selection valve into a column passing mode during step (d).

According to still another embodiment, the method may further include changing the mode of the multifunction selection valve into a titanium dioxide column passing mode, after changing the mode of the multifunction selection valve into a column passing mode.

The multifunction selection valve according to an embodiment modifies the flow path of a solvent, and thus allows a reverse-phase liquid chromatography system to realize a function of one-dimensional separation capable of desalting and sample concentration; a function of two-dimensional separation function capable of increasing separation efficiency by linking one-dimensional separation using a 1st dimension separation column with reverse-phase two-dimensional separation; and a function of on-line digestion capable of digesting proteins into peptides by generating high pressure in a solvent. Further, it is possible for a reverse-phase liquid chromatography system to realize a function of extracting phosphopeptides selectively by using a titanium dioxide column.

In addition, the fully automated multifunctional liquid chromatography system according to an embodiment may perform a function of one-dimensional separation, a function of two-dimensional separation, an on-line digestion function and a function of extracting phosphopeptides while using only one solvent feed pump.

Further, the method for analyzing a sample according to an embodiment may perform the analysis of a sample efficiently by combining a function of one-dimensional separation, a function of two-dimensional separation, an on-line digestion function and a function of extracting phosphopeptides with each other as desired through the use of the aforementioned fully automated multifunctional liquid chromatography system.

Other features and aspects will be apparent from the following detailed description and the claims.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION OF EMBODIMENTS

The advantages, features and aspects of the present disclosure will become apparent from the following description of the embodiments with reference to the accompanying drawings, which is set forth hereinafter. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Figure 1A:
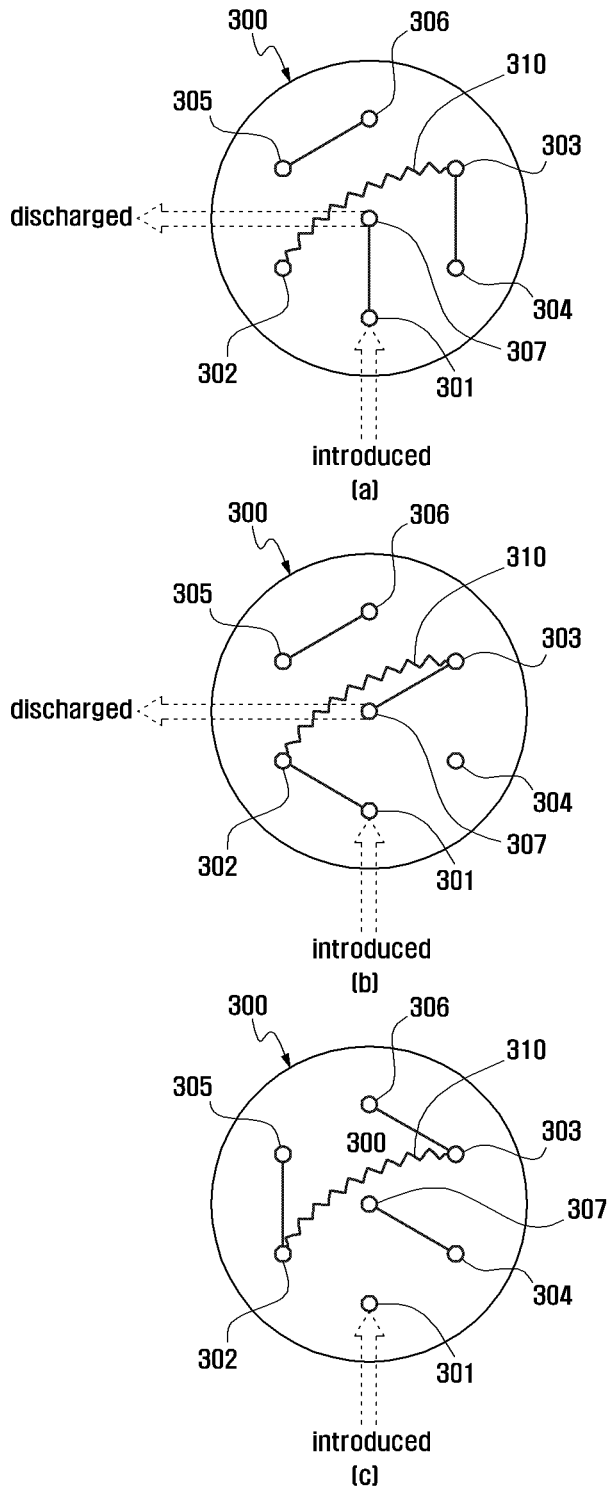
FIG. 1a is a schematic view showing different modes of the multifunction selection valve according to an embodiment.

In one aspect, there is provided a multifunction selection valve 300. As shown in FIG. 1a, the multifunction selection valve 300 includes: an inlet port 301, an outlet port 307, a first connecting port of the 1st dimension separation column 302 and a second connecting port of the 1st dimension separation column 303 linked individually to each end of the 1st dimension separation column 310, and a first selection port 304, a second selection port 305 and a third selection port 306 fluidically communicated with the other ports selectively.

The multifunction selection valve 300 may be disposed in a flow path directing from a sample inlet valve, to which a sample is injected, to a trap valve to which a reverse-phase liquid chromatography column carrying out analysis of the injected sample.

The multifunction selection valve 300 according to an embodiment may include the following three modes by modifying the connection among the ports.

The first mode is a fluid passing mode in which a fluid discharged from the sample inlet valve is introduced and discharged to a trap valve. In the fluid passing mode, as shown in FIG. 1a(a), the inlet port 301 is fluidically communicated with the outlet port 307. Herein, the second connecting port of the 1st dimension separation column 303 may be fluidically communicated with the first selection port 304, and the second selection port 305 may be fluidically communicated with the third selection port 306. Therefore, under these circumstances, the fluid introduced from the sample inlet valve is not passed through the 1st dimension separation column 310 but is discharged directly to the trap valve via the inlet port 301 and the outlet port 307.

The second mode is a column passing mode in which the fluid discharged from the sample inlet valve is passed through the 1st dimension separation column 310 and then discharged to the trap valve. FIG. 1a(b) shows the connection among the ports in the column passing mode. In other words, the inlet port 301 is fluidically communicated with the first connecting port of the 1st dimension separation column 302, and the second connecting port of the 1st dimension separation column 303 is fluidically communicated with the outlet port 307. Herein the second selection port 305 and the third selection port 306 may be fluidically communicated with each other. Therefore, the fluid introduced to the multifunction selection valve 300 is passed through the inlet port 301, the first connecting port of the 1st dimension separation column 302, the 1st dimension separation column 310, the second connecting port of the 1st dimension separation column 303 and the outlet port 307 sequentially, and then is discharged toward the trap valve.

The third mode is a fluid blocking mode in which the fluid discharged from the sample inlet valve is prevented from being introduced to the multifunction selection valve 300. As shown in FIG. 1a(c), in the fluid blocking mode, the inlet port 301 and the outlet port 307 are fluidically interrupted with each other. Therefore, the fluid discharged from the sample inlet valve is blocked at the entrance of the multifunction selection valve 300. According to one embodiment of the fluid blocking mode, the first connecting port of the 1st dimension separation column 302 is fluidically communicated with the second selection port 305, the second connecting port of the 1st dimension separation column 303 is fluidically communicated with the third selection port 306, and the first selection port 304 is fluidically communicated with the outlet port 307 in order to prevent the fluid from being introduced to the inlet port 301.

As described hereinafter, the fluid passing mode of the multifunction selection valve allows a liquid chromatography system to realize a function of one-dimensional separation, the column passing mode allows two-dimensional separation, and the fluid blocking mode allows on-line digestion including digesting proteins into peptide states by increasing the pressure of a solvent. The aforementioned number and connection of the ports are illustrative only, and the scope of the present disclosure is not limited thereto, as long as the ports may guide or close the flow path of the fluid introduced to/discharged from the multifunction selection valve.

Meanwhile, the 1st dimension separation column 310 may be any columns capable of carrying out two-dimensional separation by being combined with a reverse-phase liquid chromatography column. For example, a strong cation exchange (SCX) column, a weak anion exchange (WAX) column, a hydrophilic interaction liquid chromatography (HILIC) column, or a strong cation exchange-weak anion exchange (SCX-WAX) mixed column may be used as the 1st dimension separation column.

Figure 1B:
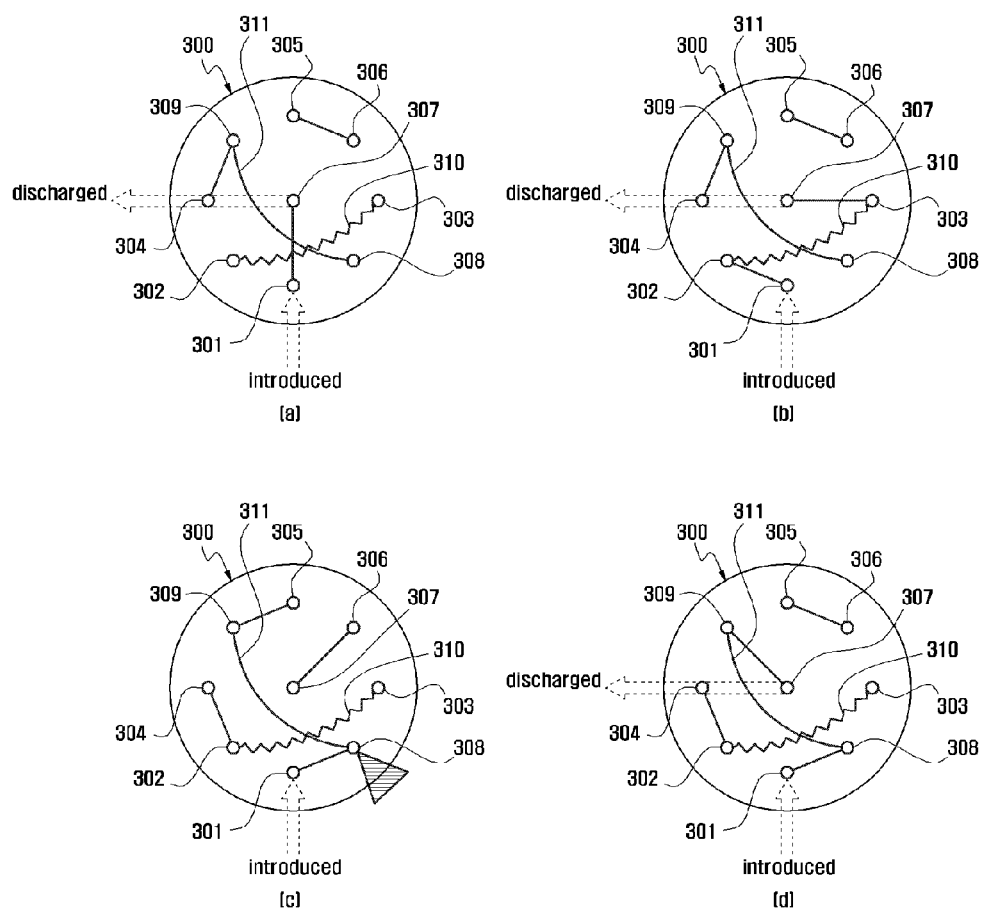
FIG. 1b is a schematic view showing different modes of the multifunction selection valve according to another embodiment.

FIG. 1b is a schematic view showing different modes of the multifunction selection valve according to another embodiment.

The multifunction selection valve as shown in FIG. 1b may be linked to a titanium dioxide column 311 in addition to the 1st dimension separation column 310. Thus, besides the aforementioned functions, it is possible to carry out selective extraction of phosphopeptides by passing the sample through the titanium dioxide column 311.

In other words, the multifunction selection valve as shown in FIG. 1b includes, in addition to the multifunction selection valve as shown in FIG. 1a, a first titanium dioxide column-connecting port 308 and a second titanium dioxide column-connecting port 309, to which both ends of the titanium dioxide column 311 are connected. Therefore, hereinafter, the multifunction selection valve of FIG. 1b will be described about its constitution different from the constitution of the multifunction selection valve of FIG. 1a.

FIG. 1b(a) shows a fluid passing mode, wherein the inlet port 301 is fluidically communicated with the outlet port 307. Referring to selection ports, the first selection port 304 is fluidically communicated with the second titanium dioxide column-connecting port 309, and the second selection port 305 is fluidically communicated with the third selection port 306.

FIG. 1b(b) shows a column passing mode, in which the inlet port 301 is fluidically communicated with the first connecting port of the 1st dimension separation column 302, and the outlet port 307 is fluidically communicated with the second connecting port of the 1st dimension separation column 303. The constitution of the selection ports is the same as FIG. 1(a).

FIG. 1b(c) shows a fluid blocking mode, in which the first titanium dioxide column-connecting port 308 is closed.

FIG. 1b(d) shows a titanium dioxide column passing mode, wherein the inlet port 301 is fluidically communicated with the first titanium dioxide column-connecting port 308, and the outlet port 307 is fluidically communicated with the second titanium dioxide column-connecting port 309. Referring to selection ports, the first selection port 304 is fluidically communicated with the first connecting port of the 1st dimension separation column 302, and the second selection port 305 is fluidically communicated with the third selection port 306.

Any combination of the selection ports may be used as long as the connection thereof allows each mode.

Hereinafter, the fully automated multifunctional liquid chromatography system including the multifunction selection valve 300 according to an embodiment will be described. The multifunction selection valve as shown in FIG. 1b may be realized while it includes all the functions of the multifunction selection valve as shown in FIG. 1a. Therefore, the following description will be based on the multifunction selection valve 300 having nine ports as shown in FIG. 1b for convenience.

Figure 2A:
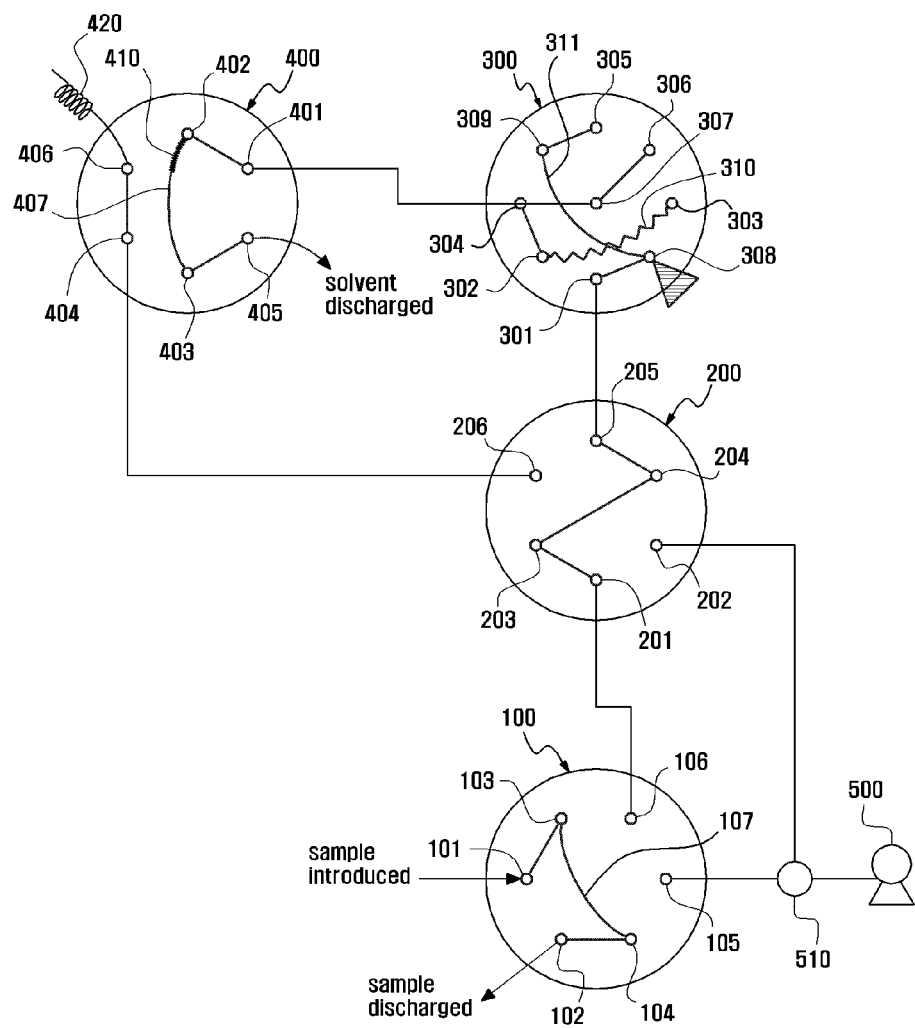
FIG. 2a is a schematic view showing the configuration of each valve during the sample injection to the fully automated multifunctional liquid chromatography system according to an embodiment.

As shown in FIG. 2a, the fully automated multifunctional liquid chromatography system according to an embodiment includes:
- a sample inlet valve 100 to which a sample to be analyzed is introduced;
- a trap valve 400 fluidically communicated with a solid phase extraction column 410 and a reverse phase liquid chromatography column 420;
- a multifunction selection valve 300 disposed in a flow path directing from the sample inlet valve to the trap valve, and linked to a 1st dimension separation column 310 and optionally to a titanium dioxide column 311; and
- a connection valve 200 supplying the fluid discharged from the sample inlet valve selectively to the multifunction selection valve 300 or the trap valve 400.

FIG. 2a is a schematic view showing the configuration of the valves during the sample injection.

The sample inlet valve 100 allows introduction of a sample to be analyzed, and includes a sample inlet port 101, a sample outlet port 102, a first sample storage loop-connecting port 103 and a second sample storage loop-connecting port 104 linked to each other by a sample storage loop 107, a solvent inlet port 105, and a solvent outlet port 106.

FIG. 2a shows the sample inlet valve during the sample injection. Herein, the sample inlet port 101 is fluidically communicated with the first sample storage loop-connecting port 103, and the sample outlet port 102 is fluidically communicated with the second sample storage loop-connecting port 104, so that the sample may be introduced to the sample storage loop 107 through the sample inlet port 101. The sample storage loop 107 allows the users to obtain a sufficient sample concentration by repeating sample injection many times if a given sample concentration is judged to be too low.

The sample storage loop 107 may have a volume of 1 μL to 10 μL. When the sample storage loop 107 has a volume less than 1 μL, sample handling may be difficult. On the other hand, when the sample storage loop has a volume greater than 10 μL, it takes too long time to inject a sample.

In addition, the sample inlet valve 100 includes a sample outlet port 102, which allows discharge of an excessive amount of sample so that the sample storage loop 107 may receive the sample in the above-specified range of volumes.

Figure 2B:
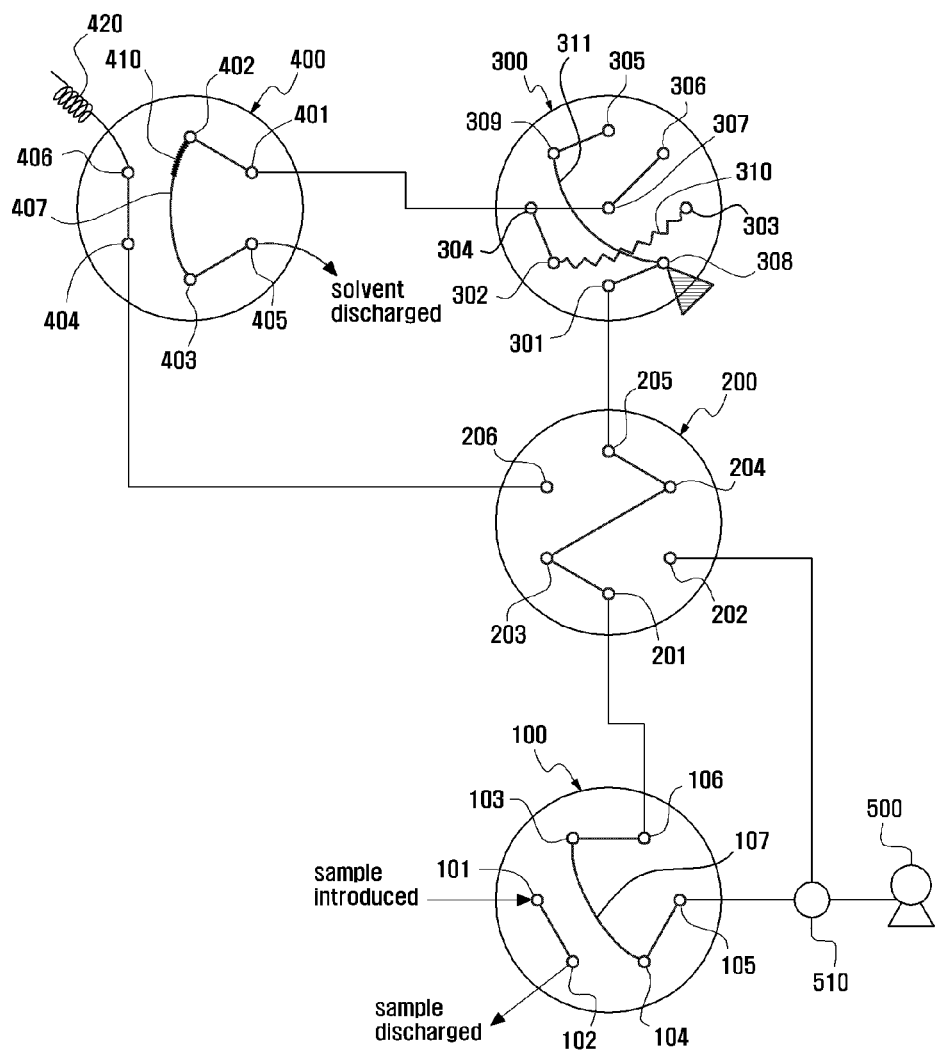
FIG. 2b is a schematic view showing the configuration of each valve during the on-line digestion carried out in the fully automated multifunctional liquid chromatography system according to an embodiment.

After completing the sample introduction as described above, a mode switch (not shown) of the sample inlet valve 100 is used to convert the operating mode from a first mode (FIG. 2a) to a second mode (FIG. 2b).

In the second mode of the sample inlet valve 100, the first sample storage loop-connecting port 103 is fluidically communicated with the solvent outlet port 106, and the second sample storage loop-connecting port 104 is fluidically communicated with the solvent inlet port 105.

The fully automated multifunctional liquid chromatography system according to one embodiment may further include a solvent feed pump 500 to supply a solvent to the sample inlet valve 100 or the connection valve 200.

The solvent feed pump 500 may supply the solvent under a pressure of 5,000 psi to 20,000 psi. When the pressure is lower than 5,000 psi, resolution may be degraded because the available length of a column is decreased. On the other hand, when the pressure is higher than 20,000 psi, the solvent may be leaked from the valve.

The solvent supplied from the solvent feed pump 500 may be a first solvent or a mixed solvent of a first solvent with a second solvent. For this, the solvent feed pump 500 is provided with a solvent selection valve (not shown) to supply either the first solvent or the mixed solvent containing the first solvent and the second solvent in a predetermined ratio. In addition, a T-shaped solvent dividing tube 501 may be linked to the solvent feed pump 500 to supply the solvent selectively to the sample inlet valve 100 or the connection valve 200.

FIG. 2b is a schematic view showing the configuration of each valve during the on-line digestion carried out in the fully automated multifunctional liquid chromatography system according to an embodiment.

The first solvent is introduced from the solvent inlet port to the sample inlet valve 100 through the solvent feed pump. Due to the hydraulic pressure of the first solvent, the sample stored in the sample storage loop 107 is discharged through the solvent outlet port 106 and arrives at the connection valve.

The connection valve 200 may include a first inlet port 201, a second inlet port 202, a first connection port 203, a second connection port 204, a first outlet port 205 and a second outlet port 206.

Since the first inlet port 201 of the connection valve 200 is fluidically communicated with the solvent outlet port 106 of the sample inlet valve 100, the first solvent introduced from the solvent feed pump is passed through the connection valve while it is passed through the first inlet port 201, the first connection port 203, the second connection port 204 and the first outlet port 205 sequentially along with the sample. Herein, as shown in FIG. 2b, the connection valve has a Z-shaped flow path formed between the ports fluidically communicated with each other.

The first solvent passed through the connection valve 200 arrives at the multifunction selection valve through the inlet port 301 of the multifunction selection valve fluidically communicated with the first outlet port 205 of the connection valve 200. Herein, each port of the multifunction selection valve 300 is in the configuration of the above-described fluid blocking mode. In other words, the inlet port 301 and the outlet port 307 are fluidically interrupted with each other by closing the first titanium dioxide column-connecting port 308. As described above, the fluid blocking mode may be realized in such a manner that the inlet port 301 and the outlet port 307 of the multifunction selection valve 300 are fluidically interrupted with each other without any particular limitation.

Therefore, the first solvent may not be passed through the multifunction selection valve 300, and thus the pressure of the first solvent increases more and more. In this manner, on-line digestion of proteins into peptide states is carried out by blocking the flow of the solvent while the solvent is conveyed to generate high pressure. In this case, on-line digestion shows higher efficiency as the solvent pressure increases. Thus, the pressure of the first solvent may be increased to the possible highest pressure of the valve.

Figure 2C:
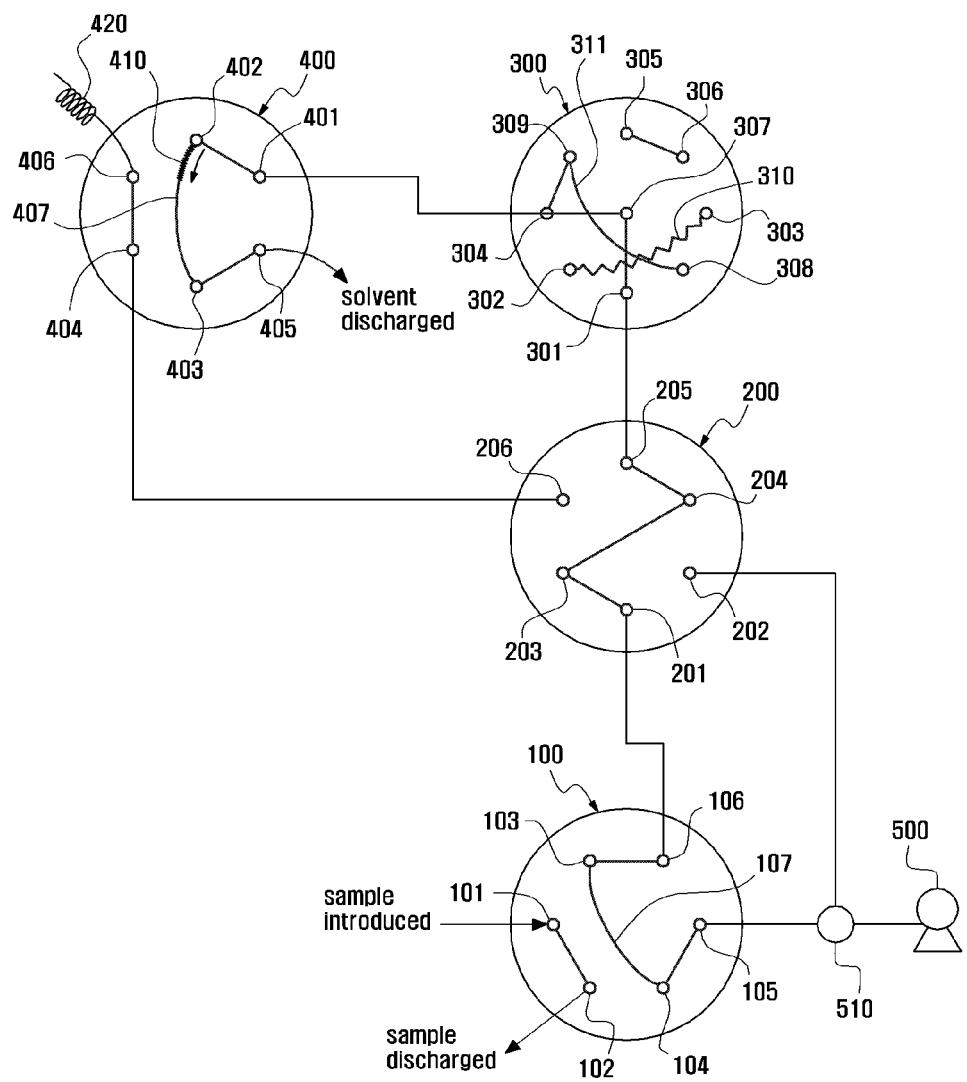
FIG. 2c is a schematic view showing the configuration of each valve during the one-dimensional separation carried out in the fully automated multifunctional liquid chromatography system according to an embodiment.

After carrying out the on-line digestion, one-dimensional separation may be carried out to perform desalting and concentration of the sample. FIG. 2c is a schematic view showing the configuration of each valve during the one-dimensional separation carried out in the fully automated multifunctional liquid chromatography system according to an embodiment.

As shown in FIG. 2c, the inlet port 301 and the outlet port 307 of the multifunction selection valve 300 are allowed to fluidically communicate with each other to perform one-dimensional separation. Therefore, the solvent introduced from the inlet port is not passed through the 1st dimension separation column 310 but is discharged to the trap valve 400 through the outlet port.

The trap valve 400 may include a solid phase extraction column-connecting port 402 fluidically communicated with the solid phase extraction column 410, a reverse-phase liquid chromatography column-connecting port 406 fluidically communicated with the reverse-phase liquid chromatography column 420, a first inlet port 401, a second inlet port 404, a sample conveying loop-connecting port 403 connected to the solid phase extraction column-connecting port via a sample conveying loop 407, and an outlet port 405. In addition, the first inlet port 401 of the trap valve 400 is fluidically communicated with the outlet port 307 of the multifunction selection valve 300.

The first solvent passed through the multifunction selection valve 300 arrives at the trap valve 400. At that time, each port of the trap valve is in such a configuration that the first inlet port 401 is fluidically communicated with the solid phase extraction column-connecting port 402, and the sample conveying loop-connecting port 403 is fluidically communicated with the outlet port 405.

Therefore, the sample conveyed together with the first solvent from the multifunction selection valve 300 is passed through the solid phase extraction column 410 through the solid phase extraction column-connecting port 402 by way of the first inlet port 401. The flow direction of the sample introduced thereto is shown by the arrow mark.

The solid phase extraction column 410 is connected directly to the solid phase extraction column-connecting port 402. The solid phase extraction column 410 has an inner diameter of 50 µm-500 µm and a length of 1 cm-4 cm. Such a length is significantly smaller than the conventional solid phase extraction columns. Since the solid phase extraction column has such a small length even though it is operated under a very high pressure of about 10,000 psi, it is possible to maximize the resolution upon separating a sample. In addition, as described hereinafter, it is possible to further improve the resolution because the sample injecting direction and the sample eluting direction to the reverse-phase liquid chromatography column are opposite to each other.

According to one embodiment, a stainless steel liner of an internal reducer is used as a solid phase extraction column 410, and a material, such as a C18 material, is packed into the column. Then, both ends of the column are closed with stainless steel screens having a pore size of about 2 µm to prevent the packing material from being discharged from the column. In this manner, a firm solid phase extraction column that may resist against such a high pressure is provided.

Meanwhile, the flow rate of the sample introduced to the solid phase extraction column 410 by the hydraulic pressure of the first solvent may be controlled through the first solvent discharged at a flow rate of 0.5 µL/min to 10 µL/min. In addition, the outlet port 405 also discharges the salt contents contained in the sample, thereby accomplishing efficient desalting.

Hereinafter, a two-dimensional separation function will be described, and the two-dimensional separation function is capable of increasing the efficiency of desalting and concentration of a sample after fractionating the sample by allowing the first solvent to be passed through the 1st dimension separation column.

Figure 2D:
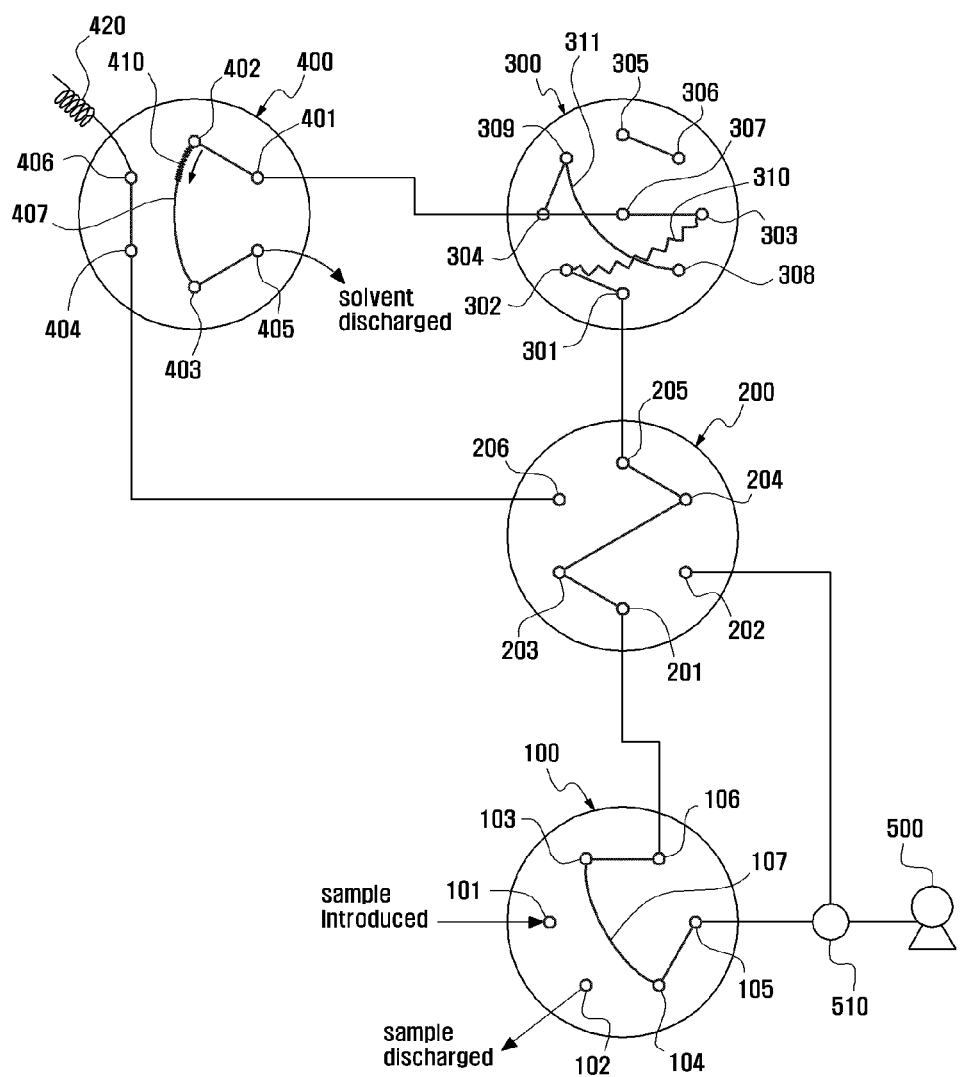
FIG. 2d is a schematic view showing the configuration of each valve during the two-dimensional separation carried out in the fully automated multifunctional liquid chromatography system according to an embodiment.

FIG. 2d is a schematic view showing the configuration of each valve during the two-dimensional separation carried out in the fully automated multifunctional liquid chromatography system according to an embodiment.

To carry out the two-dimensional separation function, the multifunction selection valve 300 is converted from a fluid passing mode into a column passing mode, while the sample inlet valve 100, the connection valve 200 and the trap valve 400 are in the same configuration as the embodiment of the one-dimensional separation function. In other words, as shown in FIG. 2d, in a column passing mode, the inlet port is fluidically communicated with the first connecting port of the 1st dimension separation column 302, and the outlet port 307 is fluidically communicated with the second connecting port of the 1st dimension separation column 303. Therefore, the first solvent introduced to the multifunction selection valve 300 is passed through the 1st dimension separation column 310 and then sent to the trap valve 400. In this manner, it is possible to further increase the efficiency of desalting and concentrating the sample after the completion of sample fractionation.

Hereinafter, a phosphopeptide extraction function will be described, and the phosphopeptide extraction function allows the first solvent to be passed through the titanium dioxide column so that phosphopeptides may be extracted selectively.

Figure 2E:
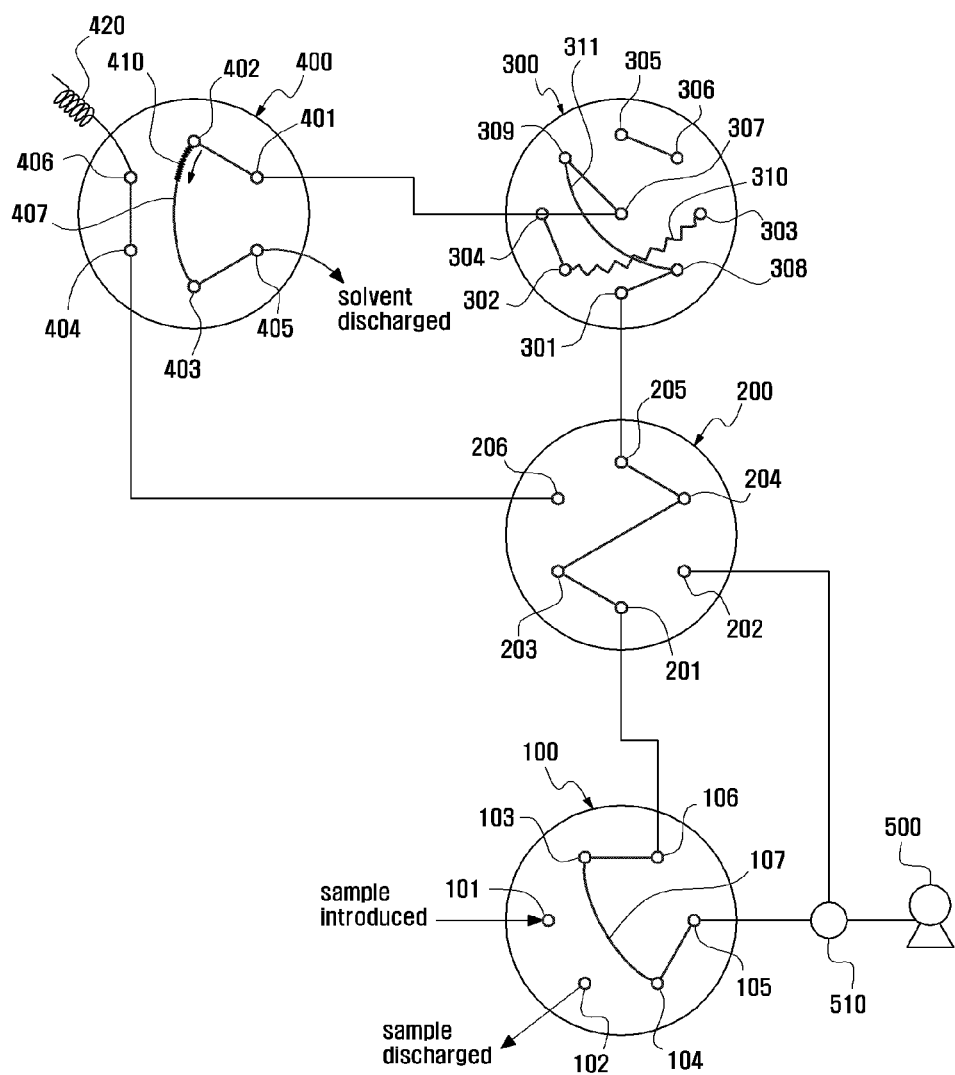
FIG. 2e is a schematic view showing the configuration of each valve during the extraction of phosphopeptides carried out in the fully automated multifunctional liquid chromatography system according to an embodiment.

FIG. 2e is a schematic view showing the configuration of each valve during the extraction of phosphopeptides carried out in the fully automated multifunctional liquid chromatography system according to an embodiment.

To carry out the phosphopeptide extraction function, the multifunction selection valve 300 is converted from a column passing mode into a titanium dioxide column passing mode, while the sample inlet valve 100, the connection valve 200 and the trap valve 400 are in the same configuration as the embodiment of the two-dimensional separation function. In other words, as shown in FIG. 2e, in a titanium dioxide column passing mode, the inlet port 301 is fluidically communicated with the first titanium dioxide column-connecting port 308, and the outlet port 307 is fluidically communicated with the second titanium dioxide column-connecting port 309. Therefore, the first solvent introduced to the multifunction selection valve 300 is passed through the titanium dioxide column 311 and then sent to the trap valve 400. In this manner, it is possible to selectively extract the phosphopeptides in the sample.

Heretofore, described was a process including introducing a sample through a sample inlet port 101 to store a predetermined amount of sample in the sample storage loop 107, and carrying out on-line digestion, one-dimensional separation and two-dimensional separation and phosphopeptide extraction of the sample by using the first solvent.

Hereinafter, a process including separating the sample introduced to the solid-phase extraction column 410 by using the second solvent and analyzing the sample will be described in detail.

Figure 2F:
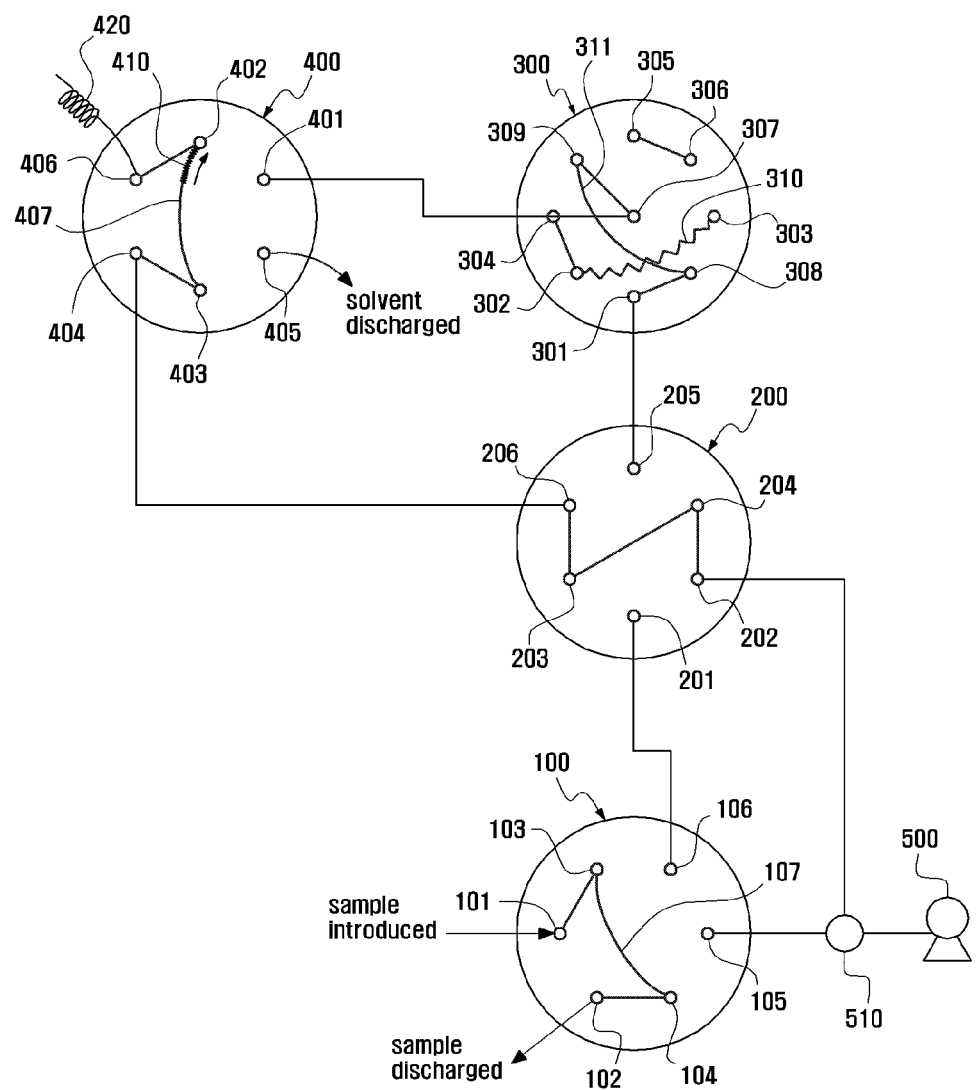
FIG. 2f is a schematic view showing the configuration of each valve during the sample analysis carried out in the fully automated multifunctional liquid chromatography system according to an embodiment.

FIG. 2f is a schematic view showing the configuration of each valve during the sample analysis carried out in the fully automated multifunctional liquid chromatography system according to an embodiment.

Referring to FIG. 2f, while the sample is analyzed, the sample inlet valve 100 is in such a condition that the solvent inlet port 105 and the solvent outlet port 106 are interrupted and the solvent introduced through the solvent dividing tube 510 may not be passed through the sample inlet valve 100 but supplied directly to the connection valve 200. In other words, during the sample analysis, each port of the sample inlet valve 100 is in the same configuration as the sample injection step.

The solvent used in the sample analysis is a mixed solvent of the first solvent with the second solvent. By varying the mixing ratio of the two solvents, it is possible to separate the sample through a solvent gradient.

In addition, in the connection valve 200, the second inlet port 202, the second connection port 204, the first connection port 203 and the second outlet port 206 are fluidically communicated with one another sequentially, so that a Z-shaped flow path is formed between the communicated ports.

The second outlet port 206 of the connection port 200 is fluidically communicated with the second inlet port 404 of the trap valve 400, so that the mixed solvent passed through the connection valve 200 may not be passed through the multifunction selection valve 300 but sent to the trap valve 400.

The trap valve 400 is subjected to a change in mode in such a manner that the reverse phase liquid chromatography column-connecting port 406 is fluidically communicated with the solid phase extraction column-connecting port 402 and the second inlet port 404 is fluidically communicated with the sample conveying loop-connecting port 403. Therefore, the mixed solvent passed through the second inlet port 404 is conveyed to the solid phase extraction column 410 by way of the sample conveying loop 407, and then is passed through the reverse-phase liquid chromatography column 420 by way of the solid phase extraction column-connecting port 402 and the reverse-phase liquid chromatography column-connecting port 406. Herein, the flow direction of the sample eluted to the reverse-phase liquid chromatography column 420 (or the flow direction of the mixed solvent) is represented by the arrow mark, which is opposite to the flow direction of the sample introduced to the solid phase extraction column (or the flow direction of the first solvent). In this manner, it is possible to further improve the resolution of sample separation.

Separation of the sample in the solid phase extraction column 410 is carried out while varying the ratio of the first solvent to the second solvent of the mixed solvent supplied from the solvent feed pump 500 with time. In other words, as the proportion of the second solvent in the mixed solvent increases, the degree of detachment of the sample attached to the solid phase extraction column 410 increases, and the sample having such an increased detachment degree is introduced to the reverse phase liquid chromatography column 420 and then is separated to perform analysis.

Various combinations of the first solvent with the second solvent may be used to accomplish the above-described purpose. As a non-limiting example, 0.1% aqueous formic acid solution and 90% aqueous acetonitrile solution may be used as the first solvent and the second solvent, respectively. In brief, such selection of solvents depends on the fact that a higher proportion of acetonitrile in the mixed solvent results in a higher degree of detachment of the sample attached to the solid phase extraction column.

The reverse phase liquid chromatography column 420 in which the sample is separated may have an inner diameter of 10 µm-150 µm and a length of 10 cm-150 cm. The reverse phase liquid chromatography column 420 is connected to a mass spectrometer for the purpose of subsequent analysis.

As described hereinbefore, the fully automated multifunctional liquid chromatography system according to an embodiment carries out a one-dimensional separation function, two-dimensional separation function, on-line digestion function and phosphopeptide extraction function, selectively as desired, by using the sample inlet valve 100, connection valve 200, multifunction selection valve 300 and trap valve 400. Although the above-described embodiment carries out all of the on-line digestion function, one-dimensional separation function, two-dimensional separation function and phosphopeptide extraction function by using the first solvent, and then carries out the sample separation and analysis by using the mixed solvent, any combinations may be used as desired. For example, in another embodiment, it is possible to perform the one-dimensional separation function alone or in combination with the two-dimensional separation function before the sample separation and analysis are carried out by using the mixed solvent. In still another embodiment, it is possible to carry out the on-line digestion first, and then the one-dimensional separation function or the two-dimensional separation function may be carried out selectively. Further, it is possible to perform the phosphopeptide extraction function in addition to each of the aforementioned functions.

EXAMPLES

The examples and experiments will now be described. The following examples and experiments are for illustrative purposes only and not intended to limit the scope of this disclosure.

Instruments

As a first solvent, 0.1% aqueous formic acid solution (available from Merck (Darmstadt, Germany)) is used. In addition, 100% acetonitrile containing 0.1% formic acid (available from J. T. Baker (Phillipsburg, N.J., USA)) is used as a second solvent.

A solid phase extraction column (75 µm ID×360 µm OD×3 cm length) is made by packing a fused silica capillary with a C18 material. After the completion of the packing, the column is subjected to ultrasonication for 5 minutes while maintaining a pressure of 12,000 psi. The column is depressurized gradually before it is used so that the C18 packing material is prevented from scattering. In addition, before packing the column, the front portion of the liner is filled with a frit packing material and the rear portion thereof is closed with a stainless steel screen (pore size: 2 µm).

A capillary column (reverse-phase liquid chromatography column) (75 µm ID×360 µm OD×80 cm length) is made by packing a fused silica capillary with slurry of C18-bound particles (Shen, Y., Moore, R. J., Zhao, R., Blonder, J., et al., *Anal. Chem.* 2003, 75, 3596-3605; Shen, Y., Tolic N., Masselon, C., Pasa-Tolic L. et al., *Anal. Chem.* 2004, 76, 144-154; Shen, Y., Smith, R. D., Unger K. K., Kumar, D., Lubda, D., *Anal. Chem.* 2005, 77, 6692-6701).

After the completion of the packing, the column is subjected to ultrasonication for 5 minutes while maintaining a pressure of 12,000 psi. The column is depressurized gradually before it is used so that the C18 packing material is prevented from scattering. In addition, before packing the column, the front portion of the liner is filled with a frit packing material and the rear portion thereof is closed with a stainless steel screen (pore size: 2 µm).

A strong cation exchange column used as an example of the 1st dimension separation column (150 µm ID×360 µm OD×15 cm length) is obtained by packing a column with slurry of a 5 µm Partisphere strong cation exchange resin (Whatman, Clifton, N.J.). After the completion of the packing, the column is subjected to ultrasonication for 5 minutes while maintaining a pressure of 10,000 psi. The column is depressurized gradually before it is used so that the packing material is prevented from scattering. In addition, before packing the column, the front portion of the liner is filled with a frit packing material and the rear portion thereof is closed with a stainless steel screen (pore size: 2 µm).

A titanium dioxide column (150 µm ID×360 µm OD×10 cm length) is obtained by packing a column with slurry of titanium dioxide particles (GL Sciences, Tokyo, Japan) having a size of 10 µm under a pressure of 5,000 psi. After the completion of the packing, the column is subjected to ultrasonication for 5 minutes while maintaining a pressure of 5,000 psi. The column is depressurized gradually before it is used so that the packing material is prevented from scattering. In addition, before packing the column, the front portion of the liner is filled with a frit packing material and the rear portion thereof is closed with a stainless steel screen (pore size: 2 µm).

Meanwhile, the reverse phase liquid chromatography column is connected to a mass spectrometer that is 7-tesla Fourier-transform ion cyclotron resonance mass spectrometer (FTICR, LTQ-FT, ThermoFinnigan) equipped with a nanoelectrospray ionization interface.

Example 1

Sample

As a sample to be analyzed, enolase isolated from bakers yeast (available from Sigma-Aldrich, St. Louis, Mo., USA) is used. The sample is pretreated by using Sequencing Grade Modified Porcine Trypsin (Promega, Madison, Wis., USA) to obtain peptides via a protein digestion process. The sample concentration is 20 ng.

Evaluation of Results

Figure 3A:
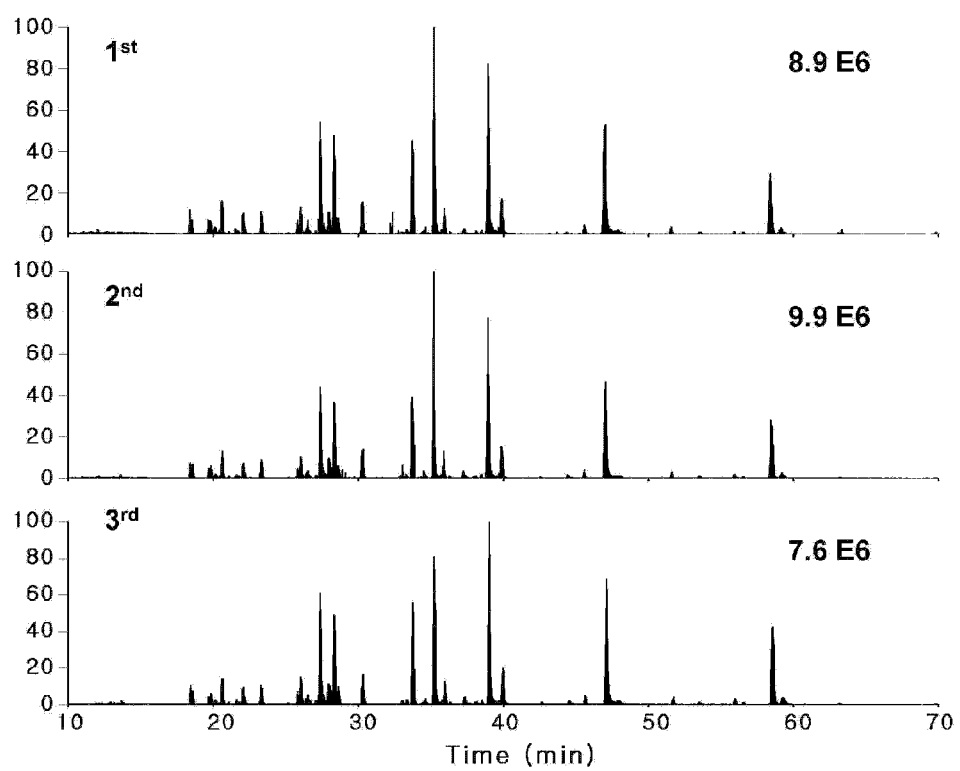
FIG. 3a and FIG. 3b show a chromatogram obtained after carrying out one-dimensional separation and two-dimensional separation of enolase peptides, respectively, by using the fully automated multifunctional liquid chromatography system according to an embodiment.

The enolase sample having a concentration of 20 ng is subjected to one-dimensional separation using the multifunctional liquid chromatography system according to an embodiment. In other words, 0.1% aqueous formic acid solution is used as a first solvent, the enolase sample is sent to the solid phase extraction column and is separated by reverse-phase chromatography. FIG. 3a is a chromatogram of the sample after separation and detection with a mass spectrometer. After carrying out the test three times, highly reproducible results are obtained. In addition, it is shown that the separation shows high resolution.

Figure 3B:
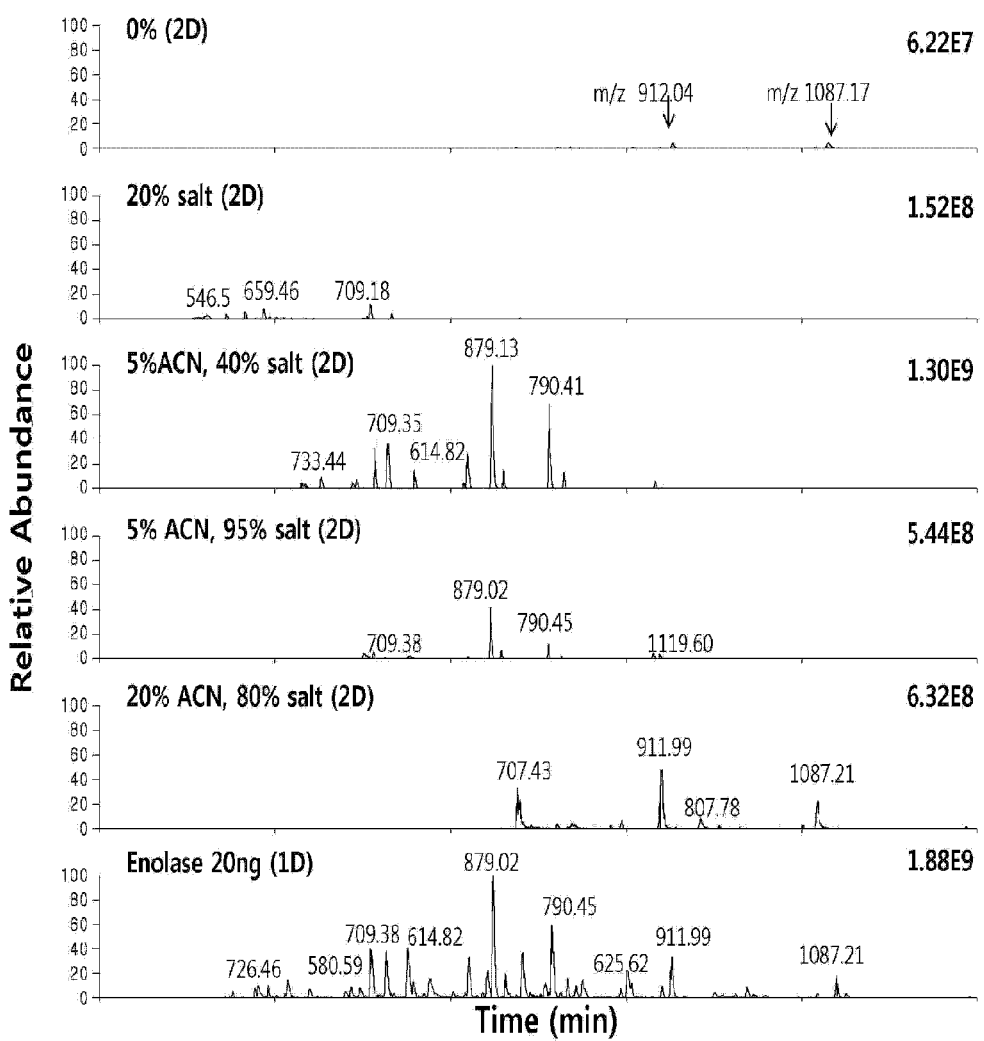

Meanwhile, FIG. 3b shows the results of the same sample after carrying out two-dimensional separation. In FIG. 3b, the upper 5 graphs show the results of two-dimensional separation using a strong cation exchange column while varying the composition of the first solvent (500 mM aqueous ammonium acetate solution, aqueous acetonitrile solution or a mixture thereof) sequentially, and the lowermost graph shows the results of one-dimensional separation. As shown in FIG. 3b, the overall results of one-dimensional separation conform to those of two-dimensional separation.

Example 2

Sample

To perform analysis of more complicated proteome samples, trypsin-decomposed peptides of whole lysate of yeast are used. The yeast proteomes used herein are haploid strains of S. cerevisiae, Y 2805 (MAT pep::his3 prb1-D1.6R can1 his1-200 ura3-52) and AF-2 (HMLa or HMRa ho ade2-1 trp1-1 can1-100 leu2-3,112 his3-11,15 ura3-1 ssd1) (Kim, M.-S., Choie, W.-S., Shin, Y. S., Yu, M. H., Lee, S.-W., *Bull. Korean Chem. Soc.* 2004, 25, 1833-1839). In this case, the proteins are dissolved into 100 mM aqueous ammonium bircabonate solution, trypsin is added thereto, and hydrolysis is carried out at 37° C. for 24 hours. The resultant products are dried completely by using SPeedVac system (SPD1010; ThermoSavant, Holbrook, N.Y., USA), and then stored at −20° C. for the subsequent experiment. The yeast peptide sample has a concentration of 20 μg.

Evaluation of Results

Figure 4A:
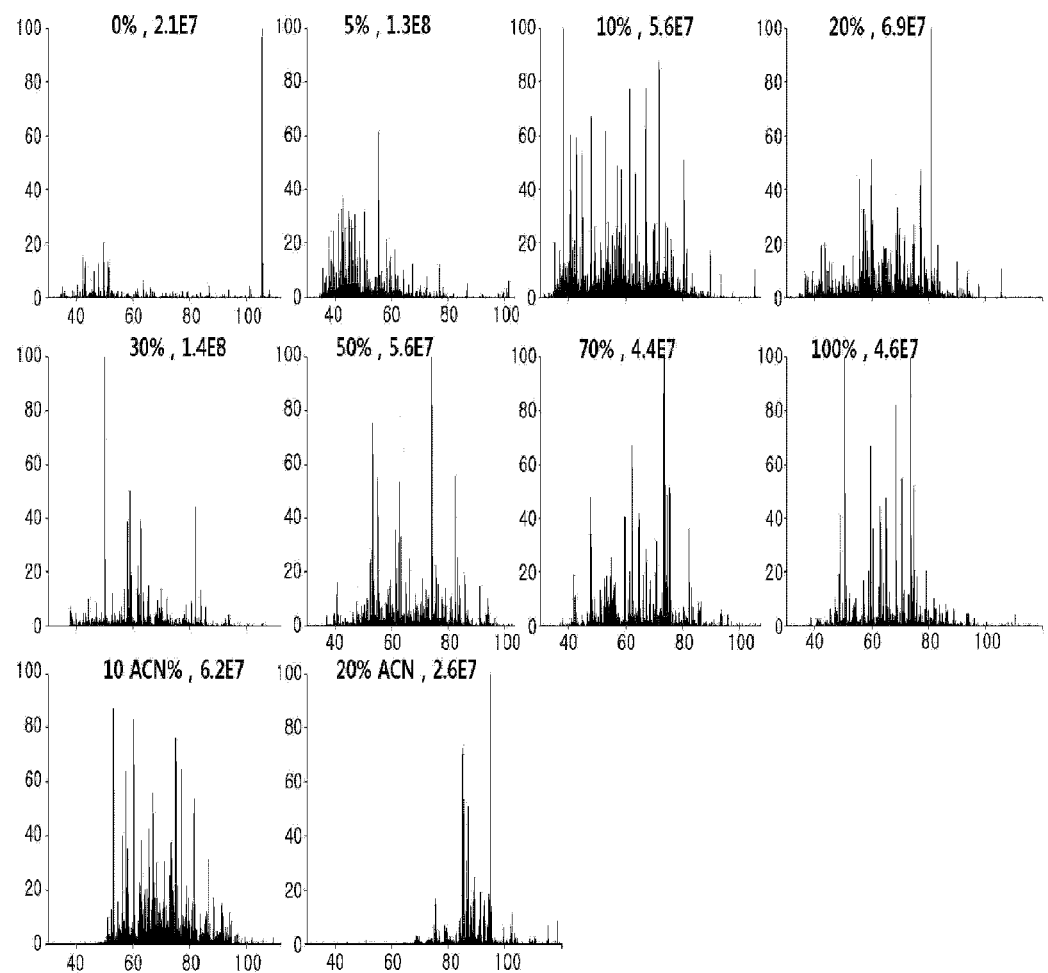
FIG. 4a and FIG. 4b show a chromatogram obtained after carrying out two-dimensional separation and one-dimensional separation of yeast peptides, respectively, by using the fully automated multifunctional liquid chromatography system according to an embodiment.
Figure 4B:
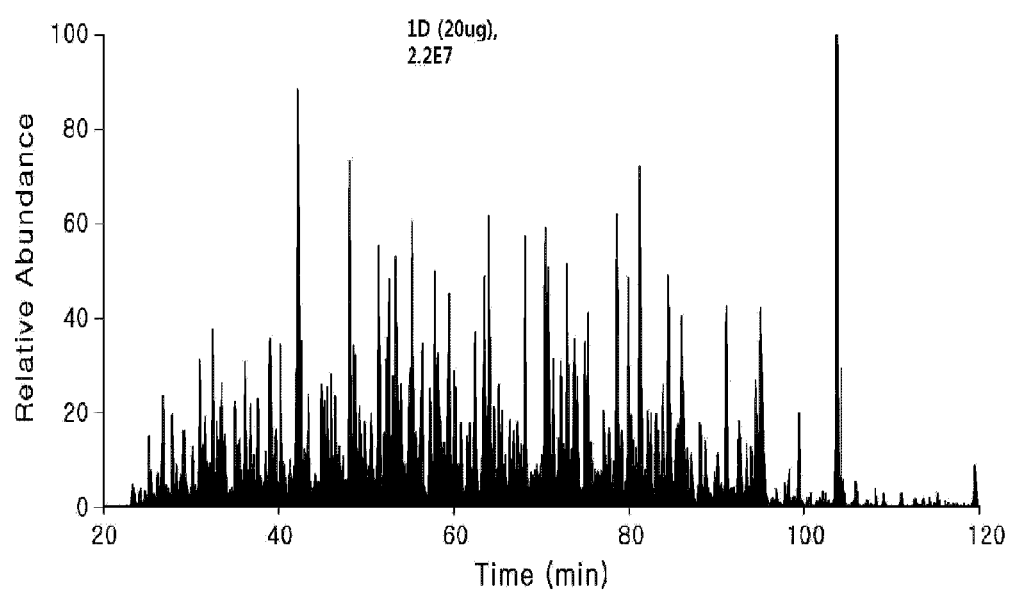

The enolase sample having a concentration of 20 μg is subjected to one-dimensional separation and two-dimensional separation using the multifunctional liquid chromatography system according to an embodiment. FIG. 4a shows the results of the same sample after carrying out two-dimensional separation using a strong cation exchange column while varying the composition of the first solvent (500 mM aqueous ammonium acetate solution, aqueous acetonitrile solution or a mixture thereof) sequentially. FIG. 4b shows the results of one-dimensional separation using a gradient in composition of 100% acetonitrile containing 0.1% formic acid as the first solvent. As compared to the results of one-dimensional separation, the results of two-dimensional separation provide a larger number of peaks in each division. This suggests that the results of two-dimensional separation allow determination of an increased number of peptides. It can be seen from the foregoing that the two-dimensional separation increases information capabilities of one-dimensional separation and improves the efficiency of analysis.

Example 3

Sample

As a sample to be analyzed, β-casein (available from Sigma-Aldrich, St. Louis, Mo., USA) is used. The sample is pretreated by using Sequencing Grade Modified Porcine Trypsin (Promega, Madison, Wis., USA) to obtain peptides via a protein digestion process. The sample concentration is 50 ng.

Evaluation of Results

Figure 5A:
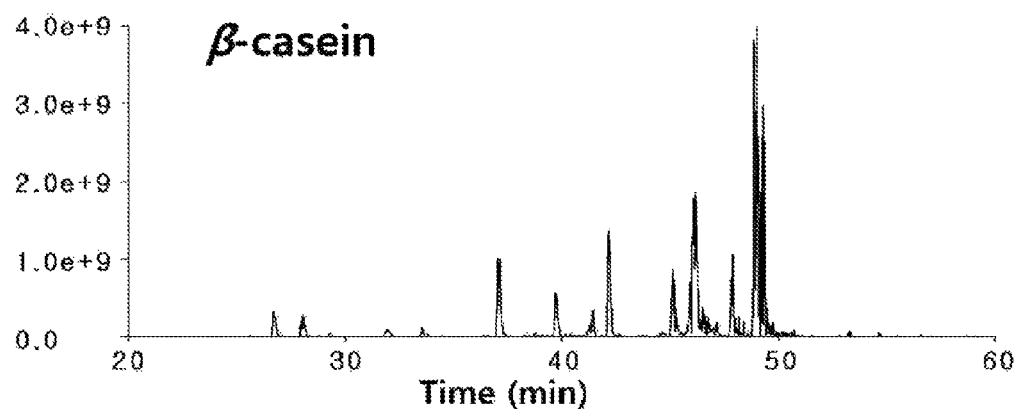
FIG. 5a and FIG. 5b show a chromatogram obtained after carrying out one-dimensional separation and phosphopeptide extraction of beta-casein peptides, respectively, by using the fully automated multifunctional liquid chromatography system according to an embodiment.
Figure 5B:
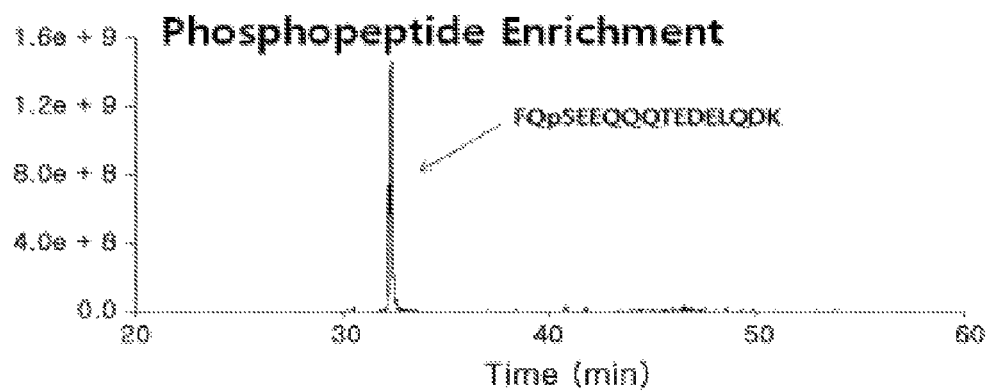

The sample is subjected to one-dimensional separation and phosphopeptide extraction using the multifunctional liquid chromatography system according to an embodiment. FIG. 5a shows the results of the same sample after carrying out one-dimensional separation using a gradient in composition of 100% acetonitrile containing 0.1% formic acid as the first solvent. FIG. 5b is a graph obtained after selective extraction of phosphopeptides, wherein the phosphopeptide extraction is carried out by passing the sample through the titanium dioxide column by using 80% acetonitrile containing 0.1% trifluoroacetic acid and lactic acid as the first solvent to allow only the phosphopeptides to be attached to the column and by eluting the phosphopeptides with 300 mM aqueous ammonium bicarbonate solution. As shown in FIG. 5a, one-dimensional separation shows the existence of the phosphopeptides but their peaks are not clear due to the other peaks. However, as shown in FIG. 5b, when passing β-casein peptides through the titanium dioxide column, only the phosphopeptides are extracted selectively.

As can be seen from the foregoing, the present disclosure provides a multifunction selection valve, a multifunctional liquid chromatography system including the valve, and a method for analyzing a sample using the system.

While the present disclosure has been described with respect to the specific embodiments, it will be apparent to those skilled in the art that various changes and modifications may be made without departing from the spirit and scope of the disclosure as defined in the following claims.

What is claimed is:

1. A multifunction selection apparatus having multiple ports to which both ends of a 1st dimension separation column are connected at a part thereof, the multiple ports comprising an inlet port, an outlet port, and a first connecting port and a second connecting port linked individually to each end of the 1st dimension separation column the multifunction selection apparatus further comprising:

a fluid passing mode in which a fluid introduced thereto is not passed through the 1st dimension separation column but is discharged, the inlet port is directly and fluidically communicated with the outlet port in the fluid passing mode;

a column passing mode in which the fluid introduced thereto is passed through the 1st dimension separation column and then discharged, the inlet port is fluidically communicated with the first connecting port of the 1st dimension separation column and the outlet port is fluidically communicated with the second connecting port of the 1st dimension separation column in the column passing mode; and a fluid blocking mode in which the fluid is prevented from being introduced, the inlet port and the outlet port are fluidically interrupted with each other in the fluid blocking mode, wherein the multiple ports further comprise a first, a second and a third selection ports;

the second selection port is fluidically communicated with the third selection port and the second connecting port of the 1st dimension separation column is fluidically communicated with the first selection port, in the fluid passing mode;

the second selection port is fluidically communicated with the third selection port, in the column passing mode; and the first connecting port of the 1st dimension separation column is fluidically communicated with the second selection port, the second connecting port of the 1st dimension separation column is fluidically communicated with the third selection port, and the first selection port is fluidically communicated with the outlet port, in the fluid blocking mode.

2. A multifunction selection apparatus having multiple ports to which both ends of a 1st dimension separation column are connected at one part thereof and both ends of a titanium dioxide column are connected at another part thereof, the multiple ports comprising an inlet port, an outlet port, a first connecting port and a second connecting port linked individually to each end of the 1st dimension separation column, and a first titanium dioxide column-connecting port and a second titanium dioxide column-connecting port linked individually to each end of the titanium dioxide column, the multifunction selection apparatus further comprising:
a fluid passing mode in which a fluid introduced thereto is not passed through the 1st dimension separation column but is discharged, the inlet port is directly and fluidically communicated with the outlet port in the fluid passing mode;

a column passing mode in which the fluid introduced thereto is passed through the 1st dimension separation column and then discharged, the inlet port is fluidically communicated with the first connecting port of the 1st dimension separation column and the outlet port is fluidically communicated with the second connecting port of the 1st dimension separation column in the column passing mode;

a fluid blocking mode in which the fluid is prevented from being introduced, the inlet port and the outlet port are fluidically interrupted with each other in the fluid blocking mode; and a titanium dioxide column passing mode in which the fluid introduced thereto is passed through the titanium dioxide column and then discharged, the inlet port is fluidically communicated with the first titanium dioxide column-connecting port and the outlet port is fluidically communicated with the second titanium dioxide column-connecting port, in the titanium dioxide column passing mode, wherein the multiple ports further comprise a first, a second and a third selection ports;

the first selection port is fluidically communicated with the second titanium dioxide column-connecting port and the second selection port is fluidically communicated with the third selection port, in the fluid passing mode;

the first selection port is fluidically communicated with the second titanium dioxide column-connecting port and the second selection port is fluidically communicated with the third selection port, in the column passing mode;

the first titanium dioxide column-connecting port is closed, in the fluid blocking mode; and the first selection port is fluidically communicated with the first connecting port of the 1st dimension separation column and the third selection port is fluidically communicated with the second connecting port of the 1st dimension separation column, in the titanium dioxide column passing mode.

3. The multifunction selection valve according to claim 1 or 2, wherein the 1st dimension separation column is any one of a strong cation exchange column, a weak anion exchange column, a hydrophilic interaction liquid chromatography (HILIC) column and a strong cation exchange-weak cation exchange mixed column.

4. A fully automated multifunctional liquid chromatography system, comprising:
a sample inlet valve to which a sample to be analyzed is introduced;
a trap valve fluidically communicated with a solid phase extraction column and a reverse phase liquid chromatography column;
a multifunction selection valve as defined in any one of claim 1 or 2, disposed in a flow path directing from the sample inlet valve to the trap valve; and
a connection valve supplying the fluid discharged from the sample inlet valve selectively to the multifunction selection valve or the trap valve.

5. The fully automated multifunctional liquid chromatography system according to claim 4, which further comprises a solvent feed pump supplying the solvent to the sample inlet valve or the connection valve, and a T-shaped solvent dividing tube is connected to the solvent feed pump to supply the solvent selectively to the sample inlet valve or the connection valve.

6. The fully automated multifunctional liquid chromatography system according to claim 4, wherein the sample inlet valve comprises a sample inlet port, a sample outlet port, a first sample storage loop-connecting port and a second sample storage loop-connecting port linked to each other by a sample storage loop, a solvent inlet port, and a solvent outlet port, and the sample inlet valve comprises:
a first mode in which the sample inlet port is fluidically communicated with the first sample storage loop-connecting port, and the second sample storage loop-connecting port is fluidically communicated with the sample outlet port; and
a second mode in which the first sample storage loop-connecting port is fluidically communicated with the solvent outlet port, and the second sample storage loop-connecting port is fluidically communicated with the solvent inlet port.

7. The fully automated multifunctional liquid chromatography system according to claim 4, wherein the connection valve comprises a first inlet port, a second inlet port, a first connection port, a second connection port, a first outlet port and a second outlet port, and the connection valve comprises:
a first mode in which the first inlet port, the first connection port, the second connection port and the first outlet port are fluidically communicated with one another in a sequential manner; and a second mode in which the second inlet port, the second connection port, the first connection port and the second outlet port are fluidically communicated with one another in a sequential manner.

8. The fully automated multifunctional liquid chromatography system according to claim 7, wherein the connection valve comprises a Z-shaped flow path formed among the fluidically communicated ports.

9. The fully automated multifunctional liquid chromatography system according to claim 4, wherein a function of one-dimensional separation of a sample is carried out, when the multifunction selection valve is in a fluid passing mode; a function of two-dimensional separation of a sample is carried out, when the multifunction selection valve is in a column passing mode; a function of on-line digestion is carried out, when the multifunction selection valve is in a fluid blocking mode; and a function of extracting phosphopeptides is carried out, when the multifunction selection valve is in a titanium dioxide column passing mode.

10. The fully automated multifunctional liquid chromatography system according to claim 4, wherein the trap valve comprises a solid phase extraction column-connecting port communicated with the solid phase extraction column, a reverse-phase liquid chromatography column-connecting port communicated with the reverse-phase liquid chromatography column, a first inlet port, a second inlet port, a sample conveying loop-connecting port linked to the solid phase extraction column-connecting port by a sample conveying loop, and an outlet port.

11. The fully automated multifunctional liquid chromatography system according to claim 10, wherein the trap valve comprises:
   a first mode in which the solid phase extraction column-connecting port is fluidically communicated with the first inlet port, and the sample conveying loop-connecting port is fluidically communicated with the outlet port; and
   a second mode in which the reverse-phase liquid chromatography column-connecting port is fluidically communicated with the solid phase extraction column-connecting port, and the second inlet port is fluidically communicated with the sample conveying loop-connecting port.

12. The fully automated multifunctional liquid chromatography system according to claim 4, wherein the solvent outlet port of the sample inlet valve is fluidically communicated with the first inlet port of the connection valve, the first outlet port of the connection valve is fluidically communicated with the inlet port of the multifunction selection valve, the outlet port of the multifunction selection valve is fluidically communicated with the first inlet port of the trap valve, and the second outlet port of the connection valve is fluidically communicated with the second inlet port of the trap valve.

13. The fully automated multifunctional liquid chromatography system according to claim 4, wherein the direction of the sample injected to the solid phase extraction column is opposite to the direction of the sample eluted toward the reverse-phase liquid chromatography column.

14. The fully automated multifunctional liquid chromatography system according to claim 4, wherein a solvent selection valve is disposed in the solvent feed pump so as to supply either a first solvent or a mixed solvent of a first solvent with a second solvent.

15. A method for analyzing a sample by using the fully automated multifunctional liquid chromatography system as defined in claim 4, the method comprising:
   (a) injecting a sample to be analyzed to the sample inlet valve;
   (b) setting the connection valve in such a mode that the sample inlet valve is fluidically communicated with the multifunction selection valve, and setting the multifunction selection valve in a fluid passing mode;
   (c) introducing a first solvent of the sample to the sample inlet valve so that the first solvent is injected to the solid-phase extraction column of the trap valve; and
   (d) changing the mode of the connection valve so that the sample inlet valve is fluidically communicated with the trap valve, and introducing a mixed solvent of the first solvent with a second solvent to the sample inlet valve so that the mixed solvent is injected to the solid-phase extraction column of the trap valve, wherein
the mixed solvent passed through the solid-phase extraction column in step (d) is further passed through the reverse-phase liquid chromatography column so that the sample is analyzed.

16. The method for analyzing a sample by using the fully automated multifunctional liquid chromatography system according to claim 15, which further comprises changing the mode of the multifunction selection valve into a column passing mode during step (c).

17. The method for analyzing a sample by using the fully automated multifunctional liquid chromatography system according to claim 16, which further comprises changing the mode of the multifunction selection valve into a titanium dioxide column passing mode, after changing the mode of the multifunction selection valve into a column passing mode.

18. A method for analyzing a sample by using the fully automated multifunctional liquid chromatography system as defined in claim 4, the method comprising:
   (a) injecting a sample to be analyzed to the sample inlet valve;
   (b) setting the connection valve in such a mode that the sample inlet valve is fluidically communicated with the multifunction selection valve, and setting the multifunction selection valve in a fluid blocking mode;
   (c) introducing a first solvent of the sample to the sample inlet valve so that the first solvent has an increased pressure;
   (d) changing the mode of the multifunction selection valve into a fluid passing mode and injecting the first solvent into the solid-phase extraction column of the trap valve; and
   (e) changing the mode of the connection valve so that the sample inlet valve is fluidically communicated with the trap valve, and introducing a mixed solvent of the first solvent with a second solvent to the sample inlet valve so that the mixed solvent is injected to the solid-phase extraction column of the trap valve, wherein
the mixed solvent passed through the solid-phase extraction column in step (e) is further passed through the reverse-phase liquid chromatography column so that the sample is analyzed.

19. The method for analyzing a sample by using the fully automated multifunctional liquid chromatography system according to claim 18, which further comprises changing the mode of the multifunction selection valve into a column passing mode during step (d).

20. The method for analyzing a sample by using the fully automated multifunctional liquid chromatography system according to claim 19, which further comprises changing the mode of the multifunction selection valve into a titanium dioxide column passing mode, after changing the mode of the multifunction selection valve into a column passing mode.

* * * * *